United States Patent [19]
Weber et al.

[11] Patent Number: 5,161,686
[45] Date of Patent: Nov. 10, 1992

[54] ODOR-ABSORBING WEB MATERIAL AND MEDICAL MATERIAL PACKAGES CONTAINING THE WEB MATERIAL

[75] Inventors: Mary G. Weber, Alpharetta; Steven W. Fitting, Acworth; Robert E. Weber, Marietta; Richard S. Yeo, Dunwoody, all of Ga.

[73] Assignee: Kimberly-Clark Corporation, Neenah, Wis.

[21] Appl. No.: 338,172

[22] Filed: Apr. 14, 1989

[51] Int. Cl.$^5$ .............................................. A61B 17/06
[52] U.S. Cl. ............................. 206/440; 128/849; 206/828; 428/283; 428/284; 428/286; 428/323; 428/331; 428/903; 428/913; 502/60
[58] Field of Search ............. 206/828, 440; 428/288, 428/284, 286, 323, 331, 913, 903, 283; 502/60; 128/849

[56] References Cited

U.S. PATENT DOCUMENTS

| | | | |
|---|---|---|---|
| 2,690,415 | 9/1954 | Shuler | 167/84 |
| 3,340,875 | 9/1967 | Dudley | 128/290 |
| 3,676,242 | 7/1972 | Prentice | 156/62.4 |
| 3,692,618 | 9/1972 | Dorschner | 161/72 |
| 3,855,046 | 12/1974 | Hansen | 161/150 |
| 3,923,592 | 12/1975 | George | 162/168 |
| 4,041,203 | 8/1977 | Brock | 428/157 |
| 4,066,395 | 1/1978 | Leonard | 8/137 |
| 4,208,459 | 6/1980 | Becker | 428/154 |
| 4,289,513 | 9/1981 | Brownhill | 55/387 |
| 4,296,166 | 10/1981 | Ogino | 428/283 |
| 4,341,213 | 7/1982 | Cohen | 128/284 |
| 4,525,410 | 6/1985 | Hagiwara | 428/198 |
| 4,701,177 | 10/1987 | Ellis | 604/385 A |
| 4,748,065 | 5/1988 | Tanikella | 428/152 |
| 4,795,482 | 2/1989 | Gioffe | 55/75 |
| 4,963,431 | 10/1990 | Goldstein et al. | 428/288 |

OTHER PUBLICATIONS

Naval Research Lab. Rept. No. 111437 [4364], Wente, submitted Apr. 15, 1954, Published May 25, 1954.
Rhom and Haas Co. brochure, "Triton X-100 Biodegradable Nonionic Surfactant", cpyrt. 1979.
Rhom and Haas Co. brochure, "Triton N-101", cpyrt. 1987.
Huggins, "Vaginal Odors & Secretions", Clin. Obs. Gyn., 24 (1981) pp. 355-377.
B. F. Goodrich brochure, "Latexes for Paper Treatment".
Rohm and Haas Co. brochure, "Rhoplex Acrylic Emulsions for Paper Saturation", cpyrt. 1977.
Air Products Co. brochure, "Vinol Polyvinyl Alcohol".

(List continued on next page.)

*Primary Examiner*—James J. Bell
*Attorney, Agent, or Firm*—Joseph P. Harps

[57] ABSTRACT

Disclosed is an odor-absorbing, non-dusting porous web material and a method of making the same. The web material includes a porous base web (for example, a fibrous base web, such as a non-woven or paper web) having distributed throughout odor-absorbing particulate (such as zeolite). Alkaline salt or alkaline earth oxide particulate, to better effect removal of acidic malodor, desirably also is distributed throughout the base web, in the final product. The odor-absorbing particulate is bound to the base web (e.g., fibers of a fibrous base web) by a binding system, containing a binding agent. The binding system, in the odor-absorbing web materials, is transparent to the odors so as not to substantially effect the ability of the particulate to absorb odor-causing material. The odor-absorbing web material is formed by dipping a porous base web in a saturant slurry containing the odor-absorbing particulate (the slurry including an alkaline salt or alkaline earth oxide) and the binding agent, together with a surfactant; squeezing out excess saturant slurry from the web; and drying. Also disclosed are two specific uses of the odor-absorbing web material: (1) in personal care products such as catamenial devices; and (2) in packages containing medical materials such as hospital gowns, which materials have been sterilized in the sealed package by gamma sterilization.

20 Claims, 3 Drawing Sheets

OTHER PUBLICATIONS

Teague Min. Prod. broch. "Sodium Bentonites & Natural Zeolites High-Tech Minerals etc." Feb. 1988, Jul. 1987, Aug. 1987.

"Potential Uses of Natural Synthetic Zeolites in Ind." D. W. Breck.

Staley Tech. Bull. No. B7, "Ethylex Gums".

Ward Worthy, "New Molecular Sieves Eliminate Odors", C&EN, May, 1988, pp. 30–31.

"UC Aiming Odor Eliminator At Personal Care Markets" Nonwovens Industry, Jun. 1988, p. 6.

Trade brochure "Now You Can Challenge the World's Most Sensitive Noses".

Zeotech Corp. brochure "Mechanism for Entrapment of Moisture and Ammonia in Zeotech Absorbent Granules".

Zeotech Corp. brochure "A Unique Mineral Ore".

Union Carbide brochure "Abscents-A New Approach for Odor Control", Gioffre, cpyrt. 1988.

U.S. Pat. Application Serial No. 136,235 filed Dec. 21, 1987 Flexible Tear Resistant Compsoite etc. no copy provided.

Chapter 1 of Zeolite Molecular Sieves, Donald W. Breck, Krieger Pub. Co., Malabar Fla., cpyrt. 1974 (rept 1984).

Chapter 9 of Zeolite Molecular Sieves, Donald W. Breck, Krieger Pub. Co., Malabar Fla., cpyrt. 1974 (rept 1984).

ODOR-ABSORBING WEB MATERIAL AND MEDICAL MATERIAL PACKAGES CONTAINING THE WEB MATERIAL

BACKGROUND OF THE INVENTION

The present invention relates to web material (e.g., fibrous web material) for absorbing odorous substances, methods for forming such material and saturant slurry compositions used for making such material. The invention is also directed to personal care products (such as sanitary napkins, tampons, diapers and incontinence pads) containing web material for absorbing odorous substances; and sterilized sealed packages containing medical materials (such as hospital gowns), wherein offensive odors upon opening the sealed packages are avoided.

Sequestration of undesired odorous substances in a non-volatile form, by adsorption or absorption on a sorbent, is a known technique. One means for providing such sequestration is to incorporate particles of a material for absorbing odorous substances (hereinafter also odor-absorbing particulate material) in a sheet-like body; the odorous substances are absorbed by the particles of sorbent material, so as to sequester the undesired odorous substances.

It has been desired to provide odor-absorbing fibrous web material (that is, fibrous sheet material for absorbing odorous substances), having odor-absorbing particulate incorporated in a fibrous base web, the web material being non-dusting (that is, wherein particulate material in the web material does not fall out after manufacture of the odor-absorbing web material). It is desired to provide odor-absorbing web material which has good odor-absorbing properties and is non-dusting, yet which can easily and inexpensively be manufactured.

Various odor-absorbing web (e.g., sheet) materials have previously been disclosed. For example, U.S. Pat. No. 2,690,415 discloses an odor-absorbing, flexible, sheet-like body which may be used in the capacity of a bandage, dressing, blanket or the like to absorb odors emanating from, for example, glandular excretions, wherein the sheet-like body contains one or more layers of granular odor-absorbing material uniformly dispersed throughout the body and secured therein (against displacement) by means of a permanently pliable adhesive. This patent discloses use of a web of open-mesh flexible woven material such as is commonly referred to as surgical gauze, the web being of open-mesh construction provided by relatively wide spacing between individual weft and warp strands, and is provided in the regions wherein the weft and warp strands overlap one another with discrete particles or masses of a permanently pliable adhesive. This patent also discloses that an exemplary adhesive includes a water-emulsion asphaltic-type of adhesive, or one of the synthetic resinous or latex base adhesives using solvents or plasticizers that may be easily evaporated or driven-off by heat treatment of the adhesive after application to the gauze web. This patent further discloses that after application of the adhesive, the odor-absorbing material in its granular form may be sprayed or sprinkled upon the adhesive-containing areas of the gauze web on one or both sides thereof, or the adhesive-containing web may be passed through a mass of the granular material to cause adherence between the individual granules of odor-absorbing material and the discrete particles of adhesive.

U.S. Pat. No. 4,289,513 discloses sorption paper (a relatively dense, non-porous paper as compared to filter paper) for absorbing odors associated with, for example, body waste devices such as sanitary napkins and disposable diapers, wherein a fibrous base paper material, which is resiliently flexible, is loaded with activated sorption particles. In its specific use for absorbing odors of body waste, the sorption paper is inserted in the sanitary napkin or diaper, to remove the odors. The sorption sheet material disclosed in U.S. Pat. No. 4,289,513 includes a fibrous base paper material which is resiliently flexible, with activated sorption particles dispersed in the fibrous base material, such particles being substantially uniformly dispersed throughout all dimensions of the fibrous base material, in an amount up to about 85% based on the weight of the base material. However, this patent does not disclose how the particles are uniformly dispersed throughout all dimensions of the fibrous base material. This patent discloses that there is a substantial absence of loose, dusty sorption particles due to use of a particular binder material, such binder material being a latex-type binder, preferably an anion polymeric emulsion of latex material (the latex materials including polyvinyl chloride copolymer, acrylics, vinylidene chlorides, acrylonitriles, vinyl acetates, polybutadiene, styrene butadiene, phenolic resins and combinations thereof). This patent further discloses that the sorption particles can include activated carbon, activated silica gel, polymeric absorbent materials, molecular sieves, ion exchange resins and other carbonaceous absorbent materials.

U.S. Pat. No. 4,525,410 discloses a fiber article having anti-bacterial properties, which article retains zeolitic particles having a bactericidal activity in fibers having fused intersection points. This patent discloses that the zeolite particles are capable of contacting with external fluids through cavities in the fibers, and that the fiber article is composed of a mixed fiber assembly including (1) natural fiber staples or synthetic fiber staples, and (2) fiber staples containing low-melting thermoplastic synthetic fibers having a melting point at least 30° C. lower than the melting point or the decomposition point of the aforesaid natural fiber staples or synthetic fiber staples. This patent discloses that at least a part of the intersection points of the staples of the mixed fiber assembly have the intersecting fibers stuck to each other by the fusion of the low-melting thermoplastic synthetic fibers. The zeolitic particles are incorporated in the fiber body by having the zeolitic solid particles contact the mixed fiber assembly while the low-melting thermoplastic synthetic fibers are in a molten state, with pressure then being applied and then the mixed fiber assembly being cooled to fix the particles onto the mixed fiber assembly.

U.S Pat. No. 4,748,065 discloses a spun-laced fabric having incorporated therein adsorbent carbonized particles, the particles being distributed over the entire fabric and dispersed throughout the cross-section of the fabric, but with more of the particles being located near the surface of the fabric, with the particles being held in place by an organic binder. This patent discloses that the fabric incorporating the adsorbent carbonized particles can be produced by brush-coating a base spun-laced fabric, on each side, with a mixture of aqueous slurries containing an aqueous slurry of activated carbon absorbent particles and an aqueous slurry of a synthetic copolymeric latex (including a polymer of ethyl acrylate and poly(vinylidine chloride/methyl acrylate/itaconic acid)).

While each of the foregoing patents describes various sheet materials for removing odors and/or noxious materials, it is desired to provide a more satisfactory odor-absorbent sheet material. In particular, it is desired to provide a more satisfactory web material that is both non-dusting and effectively removes odors, yet which can be manufactured inexpensively. It is also desired to provide such web material, which has a clean, unobtrusive appearance. It is further desired to provide such web material, which has applications in many different fields where odors arise (e.g., in refrigerators, or other enclosed spaces where there is poor exchange of fresh air).

In the previously discussed U.S. Pat. No. 4,289,513, specific applications for use of sorption paper to absorb odors are disclosed. One of the applications disclosed therein is to absorb odors emanating from devices for absorbing body liquid wastes, such as catamenial devices. Such odor can be caused by the following materials in body wastes, or formed from body wastes, absorbed in catamenial devices: (1) triethylamine; (2) pyridine; (3) furaldehyde; (4) isovaleric acid; and (5) n-propyl sulfide.

As a further area where odor is a problem, in the gamma-sterilization of medical materials (for example, hospital gowns made from polypropylene fibers) in a sealed package, an unfortunate and highly aggravating side effect of the irradiation sterilization of the polypropylene materials is that a highly offensive odor is present upon opening of the package.

Thus, in manufacturing such medical material packages, initially the medical material is made and subjected to various treatments, such as to make the materials alcohol-repellent and lint-free. The materials are then packed into a package, with the package then being sealed. Thereafter, the sealed package is subjected to gamma-irradiation sterilization, to sterilize the medical material. However, the gamma sterilization causes malodorous materials to form in the sealed package, so that when the package is opened a highly offensive odor is present. Accordingly, it is also desired to avoid the offensive odors present upon opening of the medical material-containing packages.

Thus, it is desired to provide catamenial devices, such as sanitary napkins and tampons, wherein odors emanating from such devices, due to liquid body wastes absorbed in such catamenial devices, are avoided. It is also desired to provide sealed sterilized packages, containing medical (for example, surgical) materials illustrated by hospital gowns, wherein offensive odors upon opening the sterilized packages are avoided. It is further desired to provide sterilized medical packages and catamenial devices, wherein odors emanating therefrom are avoided, while dusting of odor-absorbing particulate material (on, for example, the surgical material) is avoided. It is also desired to avoid such odors by a technique that can be provided inexpensively yet effectively, and yet which has a clean and unobtrusive appearance.

While the above-discussed documents may disclose products, processes and apparatus which exhibit some of the characteristics of the present invention, none of them discloses or suggests the present invention (including the advantages thereof), which achieves the objectives as discussed below.

SUMMARY OF THE INVENTION

Accordingly, it is an object of the present invention to provide web materials (for example, sheets or pads) for absorbing odorous substances, and a method of making such web materials.

It is a further object of the present invention to provide such web materials for absorbing odors, the webs being fibrous webs and the web materials including particulate material that absorb odorous substances.

It is another object of the present invention to provide web materials for absorbing odorous substances, including acidic odorous substances, which web materials can be inexpensively manufactured.

It is another object of the present invention to provide web materials for absorbing odorous substances, the web materials containing odor-absorbing particulate material, which web materials are non-dusting and wherein the odor-absorbing particulate material is distributed throughout the webs.

It is an additional object of the present invention to provide web materials, for absorbing odorous substances, that are non-dusting and have a pleasing white color (that is, that have a white color such that a clean and unobtrusive appearance is achieved).

It is a further object of the present invention to provide an aqueous saturant slurry to be used in making web materials for absorbing odors, the slurry including odor-absorbing particulate material and a binder for binding the odor-absorbing particulate material to the web materials (e.g., fibers of the web materials).

It is a still further object of the present invention to provide a feminine care product (for example, a catamenial device, such as a sanitary napkin or tampon), wherein odors are prevented from emanating therefrom, notwithstanding that body waste products, such as menstrual fluids, are absorbed therein.

It is yet another object of the present invention to provide packages containing sterilized medical materials, sterilized by gamma sterilization, wherein odor from the packages, upon opening the sterilized packages, is avoided.

The present invention achieves each of these objects utilizing a web material (e.g., fibrous web material) for absorbing odorous substances. The web material contains particulate material, which absorbs odorous substances, bound to a base web (e.g., fibers of a fibrous base web) by a binding system. The binding system includes a binding agent. The binding system, as part of the product (that is, as part of the final product, wherein a binding agent has been applied to the web (in a wet form) and dried, to thereby provide the binding system to bind the particulate material to the web material) is transparent to the odors (by transparent to the odors, we mean the binding system does not substantially block access to the particulate material by the odorous substances). The odor-absorbing particulate material is distributed throughout the web, thereby providing maximum efficiency of odor-absorption (that is, absorption of odorous substances). Notwithstanding binding of the odor-absorbing particulate materials to the web material, the web material has sufficient open volume so that the odorous substances can pass into contact with all of the odor-absorbing particulate.

Accordingly, a product can be provided wherein the particulate material satisfactorily binds to the web material so that the particles do not fall out of the web material (that is, the product is non-dusting). Due to use of the binding system transparent to odors, absorption of odorous substances is not adversely affected notwithstanding use of the binding system. Moreover, the bonding of the odor-absorbing particulate material to the web material maximizes surface contact between the absorbent and odorous substances, maximizing removal of the odorous substances.

The web material (for example, fibrous web material) can be any of many porous forms. For example, the fibrous web material can be a non-woven sheet (pad) of synthetic fibers, such as a spunbond web product such as described in U.S. Pat. No. 3,692,618 to Dorschner, et al. with respect to forming of filaments, and U.S. Pat. No. 3,855,046 to Hansen, et al. with respect to bonding to form the web, the contents of each of which are incorporated herein by reference in their entirety. Alternatively, the fibrous web material can be a web of meltblown fibers, formed as described in Naval Research Laboratory Report No. 11,437, dated Apr. 15, 1954 and in U.S. Pat. No. 3,676,242 to Prentice, the contents of each of which are incorporated herein by reference in their entirety. As can be appreciated, each of these forms of web material are known in the art. The web material can be a paper sheet. Moreover, the web material can be a laminate, such as a laminate of a spunbond sheet and meltblown sheet, a three-layer laminate of two spunbond sheets sandwiching a sheet of meltblown fibers, etc. The web material need not be fibrous (e.g., it can be a porous foam material). The web material itself can absorb odorous substances, thereby even further improving the product of the present invention for absorbing odorous substances.

The base web must have a void volume greater than 75%. In particular, the base web must have a large enough void volume so as to effectively be impregnated and have sufficient odor-absorbing particulate material retained therein, while still permitting effective transit of gases therethrough so as to absorb odorous substances from such gases.

The percent void volume is determined from the following equation and procedure:

$$\% \text{ Void Volume} = 1 - (d_T/d_P) \times 100$$

$d_T$ = the apparent density of the base web. This is determined by carefully weighing and measuring the length, width and thickness of a rectangular piece of the base web. The apparent density is the weight in grams divided by the volume in cubic centimeters.

$d_P$ = the absolute density of the base web. The absolute density is calculated from the weight fractions of the various fiber components and of the respective absolute densities, i.e., the reciprocal sum of the volume fractions in cubic centimeters from one gram of base web.

An essential part of the odor-absorbing web material of the present invention is odor-absorbing particulate material, incorporated in the above-described web material. The odor-absorbing particulate material is desirably a molecular sieve material, such as a zeolite (zeolite is defined in U.S. Pat. No. 4,525,410, the contents of which are incorporated herein by reference). Such zeolite can be a natural or synthetic zeolite. Use of zeolites are particularly desirable in connection with the present invention since they are white to off-white, so that sheet products having zeolite as the particulate material for absorbing odorous substances can have a clean, unobtrusive appearance. The particle size range of the zeolite is, illustratively, 1–5 microns. Other materials which can be utilized for the odor-absorbing particulate material include activated carbon, chitin and ion-exchange resins. Of course, use of activated carbon (which is black) does not provide the clean, unobtrusive appearance achieved when utilizing zeolites.

In addition to the odor-absorbing particulate material such as zeolite, the web of the present invention should also include an alkaline salt or alkaline earth oxide (both hereinafter referred to as "alkaline salt"), to provide increased removal of acidic odorous substances. The alkaline salt (in particulate form) can be bound to the fibers utilizing the same binder used for binding the, e.g., zeolite, so that both the zeolite and the alkaline salt can be incorporated in the base web material in the same processing step. As a trade-off, incorporating an alkaline salt in the base web material decreases absorption of strongly basic odorous substances, such as triethylamine (although it does not decrease absorption of weakly basic odorous substances such as pyridine).

The alkaline salts are substances that would result in a pH greater than 7.0 when in solution. As a result, acid materials react with basic salts such as:

The alkaline salt (or alkaline earth oxide) can be solubilized when applied to the web: in such case, upon drying the alkaline salt (or alkaline earth oxide) precipitates out of solution and deposits on the web material (e.g., fibers of the web material). Alternatively, the salt or oxide can be in a slurry of fine particles upon application to the web material, deposited therefrom on the web material. In either case, the particles are attached to the web by the binding system, as with the particulate material (e.g., zeolite).

An important aspect of the present invention is that the binding system, including a binding agent (the binding system binding the particulate material for absorbing odorous substances, and the alkaline salt particulate, to the web material) permits the odorous substances to pass therethrough to be absorbed in the particulate material and to permit acidic odorous substances to be removed by the alkaline salts, while still acting to bond the particulate material and alkaline salt particulate to the web material. Thus, not only is effective bonding between the web material and particulate material (and alkaline salt particulate) achieved (whereby the odor-absorbing web material is non-dusting), but also effective absorption and removal of odorous substances is achieved. Illustrative binding agents include polyvinyl alcohol; methyl cellulose; carboxy methyl cellulose; starch, including ethylated and oxidized derivatives thereof; and various polymer emulsions (latexes).

The odor-absorbing particulate material (or both odor-absorbing particulate material and alkaline salt particulate) is distributed throughout the base web material and bonded to the base web material by the binding agent. For example, where the base web material is fibrous, the odor-absorbing particulate material (and alkaline salt particulate) are bound to the fibers (along the lengths of the fibers, on the surfaces thereof). Accordingly, the total surface area of the particulate exposed for absorption is maximized, so as to maximize effectiveness of the odor-absorbing web material.

The present invention is also directed to a slurry used for applying the odor-absorbing particulate material (or such particulate material and alkaline salt particulate) to the base web. The slurry is an aqueous slurry, and includes (in addition to water) the particulate material to be deposited in the web, a wetting agent (surfactant) and the binding agent.

The present invention is also directed to a method for forming the odor-absorbing web material. Specifically, the above-described slurry is caused to impregnate the base web, and the impregnated base web is then dried.

As an illustrative technique, the base web can be dipped in the slurry (the slurry having the various components, including the odor-absorbing particulate material, uniformly distributed therethrough), with the web material (after being dipped in the slurry) being squeezed, to control the amount of material added to the base web. Desirably, the squeezing can be performed by passing the impregnated web between two rollers. Such technique of dipping the web and then squeezing by passing between two rollers facilitates a continuous process, by passing the base web from a roll thereof into the slurry and then between the two rollers, with the base web then being dried (for example, by passing over conventional steam can equipment); of course, the wet web can be air-dried, for example, at room temperature.

By the present process, the amount of material added into the base web can be controlled (both by controlling the amount of particulate material in the slurry, and by controlling the squeezing of the base web). Furthermore, a simple continuous process can be utilized for forming the odor-absorbing web material.

The present invention also provides specific applications for the odor-absorbing web material of the present invention. Specifically, according to the present invention, the odor-absorbing web material of the present invention can be incorporated in a feminine care product (for example, a catamenial device such as a sanitary napkin or tampon) so as to absorb odors and prevent such odors from emanating from such device. Various odors for which the present invention is applicable, originating in the vagina, are described in Huggins, et al., "Vaginal Odors and Secretions", Clin. Obs. Gyn., 24 (1981), pages 355-377. Illustratively, the odor-absorbing web material, containing zeolites or other odor-absorbing particulate material, and incorporated in the feminine care product according to the present invention, can absorb odorous substances such as triethylamine, pyridine, furaldehyde, isovaleric acid and n-propyl sulfide, thereby preventing such substances (and, correspondingly, their odors) from emanating from the feminine care products, and, accordingly, acting as a deodorant therein.

A further application for the odor-absorbing web material of the present invention is in a package containing medical material, such as hospital gowns. Such odor-absorbing web material absorbs odorous materials caused by gamma sterilization of the medical material, after sealing of the package. Accordingly, upon opening the sealed package, the offensive odors are avoided. The odor-absorbing web material of the present invention is inert (that is, is not functionally effected by the gamma sterilization), so that notwithstanding the presence of the odor-absorbing web material during the gamma sterilization treatment, the odor-absorbing web material can still act to absorb offensive odors in the sealed package.

Thus, the present invention achieves an odor-absorbing web material that effectively removes odorous substances and is non-dusting, yet which can be manufactured easily and in a continuous process, and can be inexpensive to manufacture. Moreover, such odor-absorbing web material can be utilized in feminine care products; and in sealed packages, containing medical materials, that have been subjected to gamma sterilization, so as to avoid odors emanating from such device and package while achieving the other objectives of the present invention.

DETAILED DESCRIPTION OF THE INVENTION

While the invention will be described in connection with specific and preferred embodiments, it will be understood that it is not intended to limit the invention to those embodiments. On the contrary, it is intended to cover all alterations, modifications and equivalents as may be included within the spirit and scope of the invention as defined by the appended claims.

The present invention contemplates a web material for absorbing odorous substances, having particulate material, which can absorb odorous substances, bound to a base web (e.g., fibrous base web) by a binding system, including a binding agent, that is transparent to the odorous substances. The odor-absorbing particulate material is distributed throughout the web material, for example, homogeneously throughout the web material.

As stated previously, in order to maximize the functional surface area of the odor-absorbing sheet material, the base (carrier) web is to have a percent void volume greater than 75%. The following Table I shows various basis weights of paper and non-woven materials, both single sheet layers and laminates, and their respective percent void volume, which can be utilized as the base web of the present invention.

TABLE I

| Void Volume Comparison | % Void Volume |
|---|---|
| 103 g/m$^2$ spunbond web | 80 |
| 68 g/m$^2$ spunbond web | 80 |
| 37 g/m$^2$ spunbond/meltblown/spunbond laminate | 81 |
| 58 g/m$^2$ spunbond/meltblown laminate | 78 |
| 45 g/m$^2$ cellulose web of softwood Kraft paper | 77 |
| 96 g/m$^2$ cellulose web of softwood | 77 |

TABLE I-continued

| Void Volume Comparison | % Void Volume |
| --- | --- |
| Kraft paper 124 g/m² cellulose web of softwood | 82 |
| Kraft paper rich in alpha pulp 184 g/m² cellulose web of softwood | 81 |
| Kraft paper rich in alpha pulp 130 g/m² cellulose web with 100% alpha pulp | 79 |

Illustratively, the base webs, when made of a nonwoven web, can have a basis weight in the range of 31-103 g/m², most preferably 38 g/m².

The most preferred base web is a laminate of spunbond/meltblown/spunbond webs, formed conventionally. The base webs can be made of, e.g., polypropylene. However, the base webs are not limited to polypropylene, and can be made of other polymer materials; e.g., other polymer materials, including thermoplastic polymers such as polyamides, polyesters, polyethylene and other polyolefins, that can be spunbond or meltblown. The webs can also be made of cellulose (for example, can be paper webs).

As indicated previously, the preferred odor-absorbing particulate materials for the present invention include zeolites, both natural and synthetic zeolites. Illustratively, natural zeolites which can be utilized include clinoptiolite, Types XY and SC supplied by Teague Mineral Products, and "Zeobrite TM", supplied by Zeotech Corp.

Synthetic zeolites include "SMELLRITE TM" and "ABSCENTS TM", each supplied by Union Carbide Corp. "ABSCENTS TM" is a pure white material with a median particle size in the range of 3-5 microns, which is insoluble in water and organic solvents and is capable of tolerating temperatures as high as 800° C. and is a preferred absorber. It can effectively remove separately contained odor-causing compounds including organic acids, aldehydes, ketones, mercaptans, ammonia and indoles. Where these odor-causing compounds are contained in combination, various of the odor-causing compounds are absorbed preferentially, and when organic acids are included in such combination with other compounds the organic acids are not absorbed efficiently.

Various zeolite materials, useful for eliminating organic odors, are described in U.S. Pat. No. 4,795,482, to Gioffre et al, the contents of which are incorporated herein by reference in their entirety.

In addition to the zeolites, ion-exchange resins, such as the "AMBERLITE®—XAD" series of ion-exchange resins, can be utilized. As indicated previously, other odor-absorbing particulate material, such as activated carbon and chitin, can be utilized; however, such materials have drawbacks, including, for example, that activated carbon is black such that the final product does not have an unobtrusive appearance. Accordingly, the desired odor-absorbing particulates are the zeolites.

As indicated previously, the odor-absorbing particulates of the present invention can include, in addition to, for example, the zeolites, various alkaline salts and alkaline earth oxides. Alkaline salts and alkaline earth oxides have a particular advantage in removing acidic odorous substances. These salts and oxides, illustratively, include the following: sodium bicarbonate ($NaHCO_3$), potassium bicarbonate ($KHCO_3$), lithium bicarbonate ($LiHCO_3$), sodium carbonate ($Na_2CO_3$), potassium carbonate ($K_2CO_3$); disodium hydrogen phosphate ($Na_2HPO_4$), sodium dihydrogen phosphate ($NaH_2PO_4$), trisodium phosphate ($Na_3PO_4$), magnesium oxide (MgO), calcium oxide (CaO), tetrasodium pyrophosphate ($Na_4P_2O_7$), tetrapotassium pyrophosphate ($K_4P_2O_7$), tetralithium pyrophosphate ($Li_4P_2O_7$), and disodium dihydrogen pyrophosphate ($Na_2H_2P_2O_7$). Of the listed alkaline salts, sodium bicarbonate is preferred. As discussed further in the following, the alkaline salt can be incorporated in the saturant slurry containing the, e.g., zeolite, for saturating the base web material.

Various binding agents used for binding the odor-absorbing particulates to the fibers will now be discussed. These binding agents can be listed in various classes, including polyvinyl alcohol, starch and latex/emulsions.

The polyvinyl alcohol binding materials are desirably partially hydrolyzed, and are preferred since they adhere to hydrophobic surfaces, have a low viscosity and low molecular weight, and have stability to gamma-radiation (as compared to latex systems, for example). A specific polyvinyl alcohol utilizable as a binder in the present invention includes "VINOL TM 205", a partially hydrolyzed (hydrolysis 87.0-89.0%) polyvinyl alcohol having a viscosity (cps) of 5-6 and a pH (in 4% aqueous solutions) of 4.5-6.5. This polyvinyl alcohol is a product of Air Products & Chemicals Co., Inc.

Starch materials which can be used as binding agents in the present invention include derivatives of starch, such as ethylated and oxidized materials. Specific illustrative starch derivatives include Penford Gums by Penford Products Company, which are derivatives of cornstarch in which hydroxyethyl groups have been substituted for hydrogens on the hydroxyl groups in the starch molecule. The Penford Gums are known gums, having known uses in the textile industry.

Illustrative latex/emulsions which can be used as binding agents according to the present invention include emulsions of acrylic polymer; styrene butadiene/rubber; nitrile/butadiene/rubber; acrylonitrile/butadiene/styrene terpolymer; vinyl chloride polymer; polyvinyl acetate polymer; and ethylene vinyl acetate polymer. Specific illustrative emulsions include known paper saturants, such as "HYCAR®" 26334 acrylic latexes and nitrile latexes, from B. F. Goodrich Co., and the "RHOPLEX®" acrylic emulsions, from Rohm & Haas Co. Of these latex/emulsions, of particular interest is "RHOPLEX®" NW-1715 acrylic emulsion.

Figure 1A:
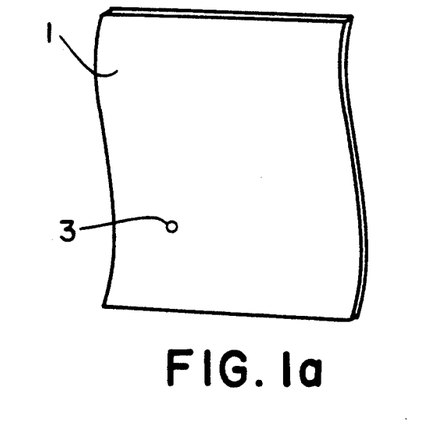
FIG. 1a shows, schematically, an odor-absorbing web material of the present invention.
Figure 1B:
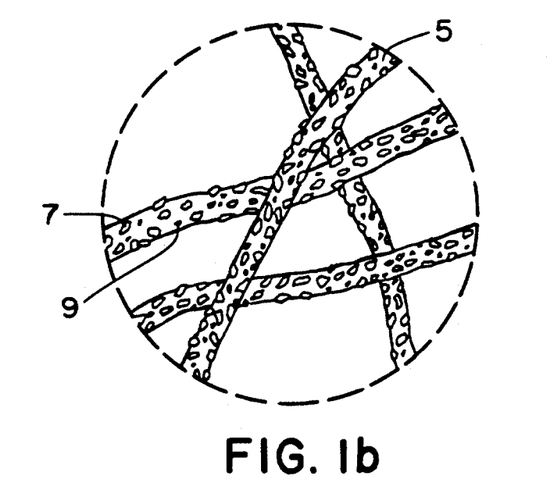
FIG. 1b shows, in detail, a portion of the web material.
Figure 2:
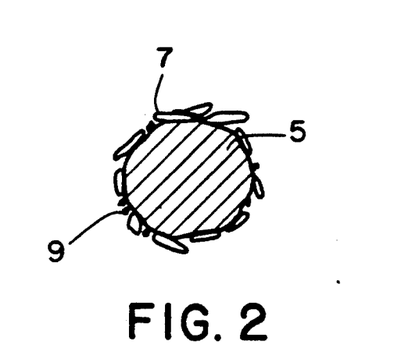
FIG. 2 shows a cross-section of a fiber, having odor-absorbing particulate material bound thereto, according to the present invention.

FIGS. 1a and 1b, and FIG. 2 illustrate the odor-absorbing material according to the present invention. FIG. 1a shows the odor-absorbing web material 1, while FIG. 1b shows, in greater detail, the fibrous material at location 3 of the web 1. As seen in FIG. 1b, the individual fibers 5 have distributed on the surface thereof along their entire length the zeolite particulate material 7 and the alkaline salt (for example, sodium bicarbonate) particulate 9, in an illustrative example. As shown in FIG. 2, the fibers 5 have the zeolite 7 and sodium bicarbonate particulates distributed around the entire circumference thereof, bound to the fibers by the binding agent.

As indicated previously, the odor-absorbing particulate material can be incorporated in the base web by dipping the base web in a saturant slurry. A saturant formulation, in general, would include a wetting agent, in addition to the particulate absorbent and the binding agent. The wetting agent (for example, surfactant), would be used to wet the saturant slurry, including particulate material, onto the base web (e.g., fibers of a fibrous base web), and would be included in the saturant slurry in amounts of 1–10% by weight of the saturant slurry. The most preferred wetting agents are "TRITON ™" surfactants, particularly "TRITON ™ X-100". The "TRITON ™" surfactants are products of Rohm & Haas Co. The X-100 brand has a common name of octylphenoxypolyethoxyethanol and is a biodegradable, non-ionic surfactant. "TRITON ™ N-101" (common name nonylphenoxypolyethoxyethanol), another product of Rohm & Haas Co., can also be utilized. Anionic wetting agents, such as sodium dioctyl sulfosuccinate, and fugative alkyl alcohols, such as isopropanol, butanol and hexanol can also be used as the wetting agent. These wetting agents (surfactants) are known wetting agents in the art.

Various saturant slurry formulations will now be set forth. Generally, the saturant slurry formulation includes in the dry formulation (apart from the water included therein), for every 100 parts by weight of particulate odor-absorbing material such as zeolite, 5–15 parts by weight of the wetting agent, 1–40 parts by weight of alkaline salt particulate, and 5–50 parts by weight of the binder; if the alkaline salt is included, such alkaline salt is preferably included in an amount of 5–40 parts by weight. More preferably, the alkaline salt is included in the saturant slurry formulation in amounts of 5–25 parts by weight.

As a specific desired formulation, the saturant includes, in dry parts, per 100 parts of, e.g., zeolite, 20 parts by weight of alkaline salt, 10 parts by weight of wetting agent and 10 parts by weight of binder.

Desirably, with a fibrous base web having a basis weight of 31–102 g/m² (ideally, 38 g/m²), the pick-up of saturant (in dry weight) on the base sheet would be 15–75 parts by weight per 100 parts by weight of fiber.

Specific saturant formulations, including water, the respective saturant formulations including "ABSCENTS ™" and activated carbon, respectively, will now be set forth in Table II. In this Table II, the activated carbon of the activated carbon dispersant was provided by milling for one hour, prior to incorporation in the saturant slurry. In the following Table II, the % solids are % by weight, while the dry and wet amounts are parts by weight.

TABLE II

| | % by weight Solids | Parts by Weight Dry | Parts by Weight Wet |
|---|---|---|---|
| "ABSCENTS ™" Saturant | | | |
| Water | | | 300 |
| 1 "TRITON ™ X-100" solution | 10 | 10 | 100 |
| 2 "ABSCENTS ™" | 100 | 100 | 200 |
| 3 "VINOL ™" 205 solution | 10 | 10 | 100 |
| Sodium bicarbonate | 100 | 20 | 20 |
| Totals | 22.6* | 140 | 620 |

*Assuming base web of 96 g/m² cellulose web of softwood Kraft paper or laminate of spunbond/meltblown. The % by weight add-on was 29%.

| Activated Carbon Saturant | | | |
|---|---|---|---|
| Water | | | 100 |
| 1 "TRITON ™ X-100" solution | 10 | 10 | 100 |
| Activated carbon dispersion | 20 | 100 | 500 |
| 3 "Vinol ™" 205 solution | 10 | 10 | 100 |
| | 15* | 120 | 800 |

*Assuming base web of 96 g/m² of a cellulose web of softwood Kraft paper. The % add-on was 17% by weight.

| "ABSCENTS ™" Saturant | | | |
|---|---|---|---|
| Water | | | 427.3 |
| 1 "TRITON ™ X-100" | 20 | 1 | 5.0 |

TABLE II-continued

| | % by weight Solids | Parts by Weight Dry | Parts by Weight Wet |
|---|---|---|---|
| solution | | | |
| 2 "ABSCENTS ™" | 100 | 100 | 100.0 |
| 4 "RHOPLEX ®" NW 1715 | 44 | 10 | 22.7 |
| | 20* | 111 | 555.0 |

*Assuming base web of cellulose web of softwood Kraft paper, with a dry add-on of 31% by weight.
¹Product of Rohm & Haas Co.
²Product of Union Carbide Corp.
³Product of Air Products & Chemicals Co., Inc.
⁴Product of Rohm & Haas Co.

As indicated previously, the saturant slurry is incorporated in the base web by dipping the base web material in the saturant slurry. Of course, care should be taken to ensure that the odor-absorbing particulate (such as zeolite), as well as the other components of the slurry, is uniformly and homogeneously dispersed throughout the saturant slurry during use of such slurry for incorporating material in the base web material. Conventional means (e.g., vibrating the slurry) can be used to ensure such homogeneous and uniform dispersion.

Figure 3:
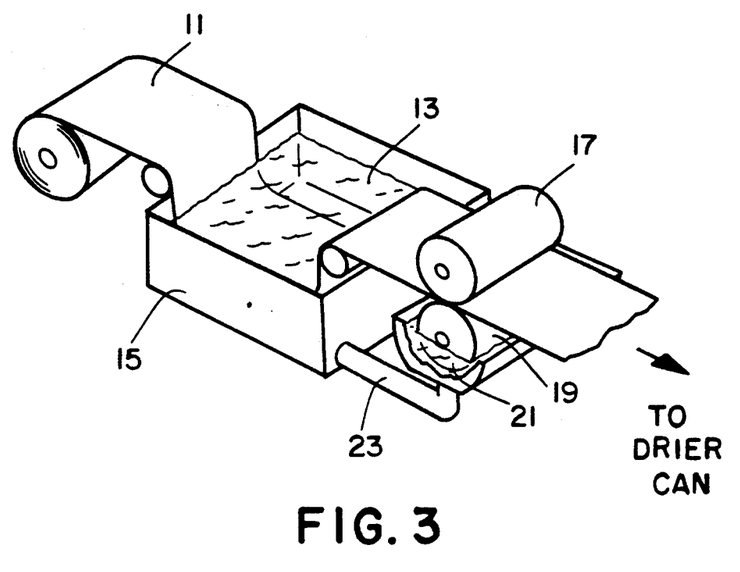
FIG. 3 is a schematic view of apparatus for impregnating the base web with saturant slurry and for controlling the amount of material added to the base web.

FIG. 3 shows, schematically, how the base web can be dipped into the saturant slurry, and then squeezed, to squeeze out slurry material, so as to control the material added-on into the web. Specifically, base web 11, in a continuous (roll) form, is dipped into the saturant slurry 13 in container 15, and then after passage out of the slurry, is passed between rollers 17 and 19 for squeezing excess slurry from the base web, to control add-on. Specifically, the rollers 17 and 19 are respectively a silicone rubber roller and a stainless steel roller. The silicone rubber roller has a Shore hardness of 60 (A scale), illustratively. The nip pressure between the two rollers illustratively ranges between 1.5–2.5 lbs./lineal inch, so as to squeeze out excess slurry.

As is clear from FIG. 3, the excess slurry squeezed out of the web material passes into tank 21, and then is transferred back into the bath 13, in tank 15, through pipe 23. After the web material passes between the two rollers, it can then be dried. Desirably, the material is dried over conventional steam cans. However, use of such steam cans is not required, and the web material impregnated with saturant can be air-dried.

Upon drying, the odor-absorbing web material, having odor-absorbing particulate material (such as zeolite), with an alkaline salt particulate, bound uniformly throughout the base web, can be cut into desired sizes for intended final use.

Shown in the following Table III is the percentage of odor reduction provided utilizing a synthetic zeolite in powder form versus such zeolite incorporated in a base web.

In Table III, as well as the following tables showing absorbing ability of various odor-absorbing web materials, absorbing ability was determined using a gas chromatography headspace analysis, described in the following. Using a volatile mixture of 100 μl pyridine, 100 μl n-propyl sulfide, 100 μl furaldehyde, 100 μl triethylamine, and 200 μl isovaleric acid, a 10 μl volume of such mixture was introduced by a pipetman, into a 40-ml EPA sample vial and sealed with a mininert screw cap. This serves as a blank to ensure the presence of all components of the volatile mixture.

A known quantity of material to be tested is placed in a 40-ml EPA vial. After the addition of 10 μl of the mixture described above the vial is sealed with a minin-ert screw cap and is incubated at 37° C. for 4 hours. (When testing a sheet form, an untreated sheet acts as the control and is run under these same conditions.) After 4 hours incubation a 10 μl headspace sample from each vial is injected into the GC using the parameters listed in the following. The area count was recorded at each retention time and percent absorption calculated.

Calculations

Calculation of percent absorption:

$$\frac{\text{Total Area of Control} - \text{Total Area of Sample}}{\text{Total Area of Control}} \times 100$$

The processing parameters for the gas chromatography (GC) are as follows:

| | |
|---|---|
| Initial Time = | 1.00 minutes |
| Initial Temp. = | 35° C. |
| Rate = | 10°/minute |
| Final Temp. = | 75° C. |
| Final Time = | 0.15 |
| Inj. B = | 175° C. |
| Det. B = | 300° C. |
| Oven Max. = | 300° C. |
| Equib. Time = | 0.15 |
| Flow B (He) = | 15.0–16.0 |
| Range (Sig. 1) = | 4 |
| Zero (Sig. 1) = | 2 |
| Attn. (Sig. 1) = | 2 |

The results in the following Table III indicate that the surface area in a sheet form is more efficient than the surface area in a powder form (not attached to a carrier web) for removing odorous substances.

TABLE III

| | Sheet Form v. Powder Form % Odor Reduction | |
|---|---|---|
| Test Material Volatiles | 113 mg Absorbent System** in Sheet Form*** | 108 mg Absorbent System** in Powder Form |
| Triethylamine | 100% | 48% |
| Pyridine | 100% | 73% |
| Furaldehyde | 100% | 81% |
| Isovaleric Acid | NR* | NR* |
| n-Propyl sulfide | 98% | 72% |

*NR = no reduction
**Absorbent System contains 100 parts synthetic zeolites, 10 parts non-ionic wetting agent, 10 parts polyvinyl alcohol.
***Cellulose web of softwood Kraft paper Tables IV–VI show odor-absorption results, using various odor-absorbing web materials according to the present invention.

TABLE IV

| | ABSORBENT SYSTEM** IN SHEET FORM containing sodium bicarbonate with various binder ratios | | |
|---|---|---|---|
| Article | 3:1 (absorbent:binder) 196 mg Absorbent System** in Sheet Form (%) | 5:1 (absorbent:binder) 195 mg Absorbent System** in Sheet Form (%) | 10:1 (absorbent:binder) 205 mg Absorbent System** in Sheet Form (%) |
| Triethylamine | NR | 72 | NR |
| Pyridine | 69 | 90 | 78 |
| Furaldehyde | 97 | 99 | 99 |
| Isovaleric Acid | 94 | 85 | 61 |
| n-Propyl sulfide | 21 | 55 | 46 |

*NR = No reduction
**Absorbent system contains 100 parts synthetic zeolite; 10 parts nonionic wetting agent; and amounts of polyvinyl alcohol to provide the specified absorbent:binder ratio in a spunbond/meltblown/spunbond laminate The results shown here are the gas chromatography headspace analysis results to determine the % of odor reduction in web composites containing synthetic zeolite with sodium bicarbonate at various ratios of binder. This diagram illustrates the absorbing nature of the sheet form at various binder ratios. The binding system is shown to be transparent to odors having 10%–30% binder. As can be seen, the 10% and 20% odor reduction is similar while beginning at 30% the reduction of the sulfide, for example, is being lost.

TABLE V

| | ABSORBENT SYSTEM** IN SHEET FORM of nonwoven web laminate with or without NaHCO₃ | |
|---|---|---|
| Volatiles | 202 mg Absorbent System** in Sheet Form (%) | 195 mg Absorbent System** in Sheet Form + 20% NaHCO₃ (%) |
| Triethylamine | *NR | 29 |
| Pyridine | 93 | 95 |
| Furaldehyde | 98 | +99 |
| Isovaleric Acid | *NR | 64 |
| n-Propyl Sulfide | 87 | 83 |

*NR = No reduction
**Absorbent system contains 100 parts synthetic zeolite; 10 parts nonionic wetting agent; 20 parts polyvinyl alcohol in a spunbond/meltblown/spunbond laminate The results shown are the gas chromatography headspace analysis to determine odor reduction of web composites containing a synthetic zeolite only, and a 5:1 ratio of synthetic zeolite to sodium bicarbonate. The advantage of the zeolite/NaHCO₃ system is the removal of acidic odors. In this example the reduction of both the acid and the base has increased with the addition of the sodium bicarbonate.

TABLE VI

| | ABSORBENT SYSTEM** IN SHEET FORM of softwood Kraft paper, with or without NaHCO₃ | |
|---|---|---|
| Volatiles | 108 mg Absorbent System** in Sheet Form (%) | 103 mg Absorbent System** in Sheet Form + 20% NaHCO₃ (%) |
| Triethylamine | 63 | NR* |
| Pyridine | 65 | 75 |
| Furaldehyde | 73 | 95 |
| Isovaleric Acid | NR* | 84 |
| n-Propyl Sulfide | 85 | 92 |

*NR = No reduction
**Absorbent system contains 100 parts synthetic zeolite; 10 parts nonionic wetting agent; 10 parts polyvinyl alcohol in a cellulose web of softwood Kraft The results shown are the gas chromatography headspace analysis to determine odor reduction of web composites containing a synthetic zeolite only, and a 5:1 ratio of synthetic zeolite to sodium bicarbonate. The advantage of the zeolite/NaHCO₃ system is the removal of acidic odors. The decrease in the reduction of the triethylamine odor is not unexpected because it is a strong base. The weaker base, pyridine is strongly absorbed.

Figure 4:
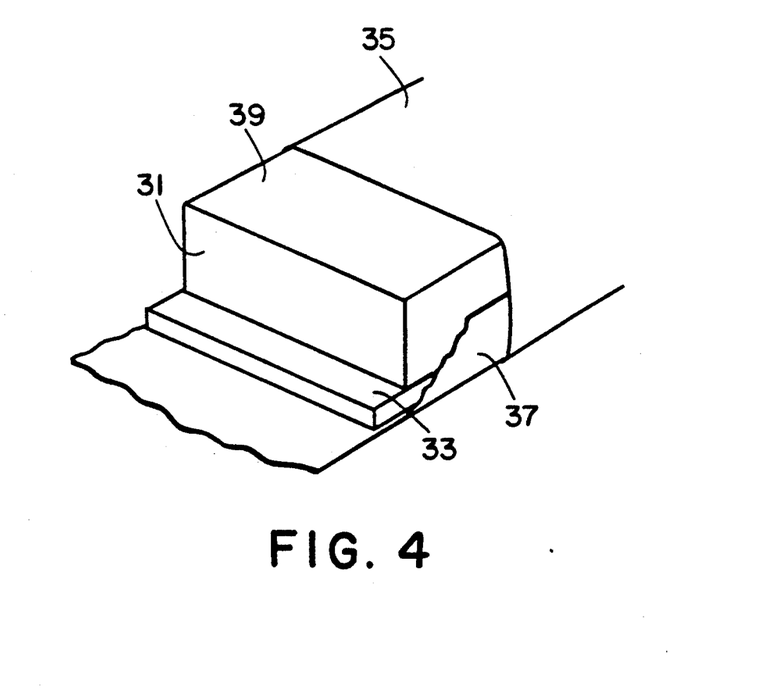
FIG. 4 schematically illustrates the absorbing portion of a sanitary napkin according to the present invention.

As indicated previously, the odor-absorbing web material of the present invention can be incorporated in catamenial devices in order to prevent odors emanating therefrom. A schematic illustration of the absorbing portion of a catamenial device (e.g., sanitary napkin) according to the present invention, including placement of the odor-absorbing web material of the present invention, is shown in FIG. 4. Specifically, the illustration shown would have the top adjacent to the body. The fluff (absorbent material 31) would be located inside a tissue layer 39, with an outer cover 35 surrounding the entire structure, the outer cover adjacent the tissue layer surrounding the fluff being adjacent the body. On the side of the fluff furthest from the body is disposed odor-absorbing web material 33. It is preferred that web 33 be disposed on the side of the fluff away from the body, or in the fluff but positioned at a location therein with most of the fluff between the body and web 33, so as to avoid contact of the web with, e.g., body waste fluids. By locating the web in the feminine care product, an effective deodorizer can be provided.

Also shown in FIG. 4 is baffle 37 positioned on the side of the odor-absorbing web material away from the body. Such baffle is provided to avoid any transmission of waste body fluids to the outside.

In the foregoing, each of the fluff material, the outer cover, the baffle and the tissue layer are conventional; location of such components are also conventional. The present invention provides use of the odor-absorbing web material, positioned as set forth in the foregoing, to achieve effective deodorant protection.

The odor-absorbing web material according to the present invention can also be used as part of a tampon. Illustratively, a tight roll of odor-absorbing web material of the present invention could be contained in the core of the tampon, and would be surrounded by the conventional absorbing material such as cotton fiber and/or rayon.

Through use of the odor-absorbing web material of the present invention, the following odorous substances can effectively be absorbed and prevented from emanating from the catamenial device: triethylamine, pyridine, furaldehyde, isovaleric acid and n-propyl sulfide.

As indicated previously, the odor-absorbing web material of the present invention can be incorporated in a package with medical materials, with the medical materials being sterilized by gamma sterilization treatment in the sealed package; the odor-absorbing web material prevents highly offensive odors emanating from the package upon opening the sealed package. The odor-absorbing material of the present invention is substantially inert to the gamma sterilization treatment (for example, treatment at 3.0–3.5 megarads, specifically 3.2 megarads) and can perform its odor-absorbing function even after being in the package that has been subjected to the sterilization treatment. Moreover, due to the non-dusting nature of the product of the present invention, upon opening of the sterilized package, the medical material (for example, hospital gown) does not, undesirably, have particulate material, from the odor-absorbing web material, thereon. The use of the odor-absorbing web material in the medical package according to the present invention absorbs the following odorous substances: acetic acid, butyric acid, isobutyric acid and propionic acid.

Figure 5:
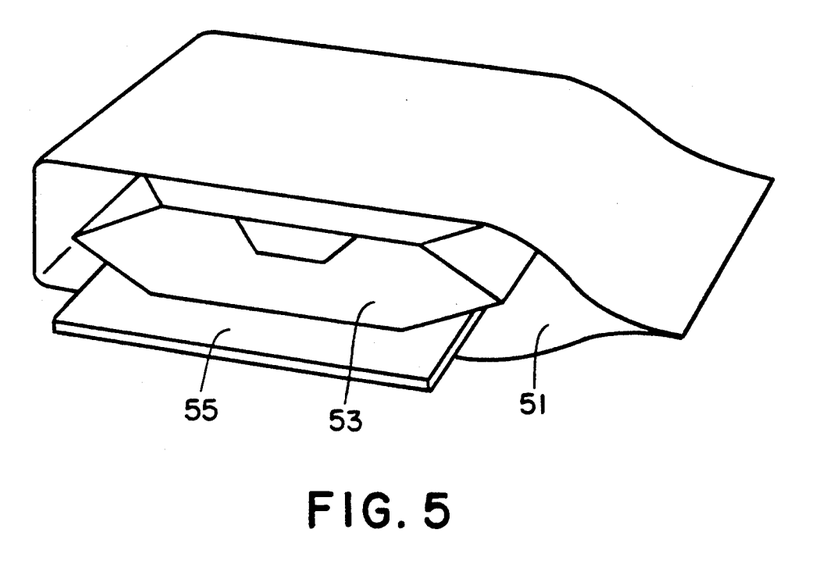
FIG. 5 shows a medical package according to the present invention.

FIG. 5 shows a side view of an open package of medical material and odor-absorbing sheet material according to this aspect of the present invention. The pack 51 contains a wrapped surgical gown 53 and an odor-absorbent web material 55 of the present invention. As shown in FIG. 5, the odor-absorbent web material is placed at the bottom of the package, between the wrapped surgical gown and the inner side of the package. However, placement of the web material in the package is optional, and it can be at the top of the package, between the top of the wrapped surgical gown and the inner side of the package.

The following Examples illustrate the present invention. While illustrative, they do not limit the present invention, which is defined by the full scope of the appended claims and equivalents thereof.

EXAMPLE 1

Two spunbond webs were formed from a fiber grade polypropylene polymer resin obtained from Exxon Corp. The webs had an average basis weight of 11 $g/m^2$ and an average filament diameter greater than 10 microns.

In order to form a spunbond/meltblown/spunbond laminate, each of the spunbond webs was joined to opposite sides of a meltblown web formed from a fiber grade polypropylene polymer resin supplied by Exxon Corp. The meltblown web had an average basis weight of 17 $g/m^2$, and an average filament diameter of less than 10 microns, and is well known as exemplified by U.S. Pat. No. 3,676,242, the contents of which are incorporated herein by reference. The three layers prepared were then laminated through spot bonding using heat and pressure, according to U.S. Pat. No. 4,041,203. The laminate had a total basis weight of 39 $g/m^2$ and had a void volume of 81%.

The palindromic laminate was then passed through a saturant slurry which was maintained at ambient conditions using a dip and squeeze technique.

The components of the saturant slurry were 77.4% by weight water, 16.1% by weight of a synthetic zeolite which may be obtained from Union Carbide Corp. under the designation of "ABSCENTS TM", 3.2% by weight of sodium bicarbonate of 99–100% purity, 1.6% by weight of a non-ionic wetting agent composed of octylphenoxy polyethoxyethanol which contains 9–10 mole of ethylene oxide units, the wetting agent being obtained from Rohm & Haas Co. under the designation of "TRITON TM X-100", and 1.6% by weight of a partially hydrolyzed (87–89% hydrolyzed) low viscosity polyvinyl alcohol obtained from Air Products & Chemicals Co., Inc., under the designation of "VINOL TM 205".

The saturated laminate was then dried by passing the laminate over a steam can having a can pressure of about 6 psi. Upon weighing, it was determined that the dried, saturated laminate had a saturated loading of about 26 $g/m^2$. That is, the weight of materials adhering to the laminate was 67% by weight of the laminate prior to its passing through the saturant slurry.

EXAMPLE 2

Two 10 $g/m^2$ continuous filament thermoplastic polypropylene webs were prepared and then laminated to a middle layer constructed of 17 $g/m^2$ microfiber meltblown polypropylene having an average filament diameter of less than 10 microns through spot bonding using heat and pressure according to U.S. Pat. No.

4,041,203. The tri-laminate of spunbond/meltblown/spunbond had a total basis weight of 37 g/m², and has a void volume of 81%.

The bonded laminate was then saturated using a dip and squeeze size press configuration, with a saturant slurry comprised, in percent by weight, of 80% of water, 14.3% by weight of an odor absorbing 200 mesh natural zeolite which may be obtained from Zeotex Corp. under the designation of "Zeobrite TM", 2.9% by weight of sodium bicarbonate, 1.4% dry weight of an emulified polymeric acrylic latex which may be obtained from B. F. Goodrich under the trade designation of "Hycar®" 26334, 1.4% by weight of a non-ionic wetting agent obtained from Rohm & Haas Co. under the designation of "Triton TM X-100". The saturated laminate was then dried by passing the laminate over a steam can with a can pressure of 6 psi.

Upon weighing, it was determined that the dried saturated web had a saturant loading of about 25 g/m². That is, the weight of the material adhering to the web was 67% by weight of the web prior to its passing through the saturant slurry.

EXAMPLE 3

A 20 g/m² continuous filament thermoplastic polypropylene spunbond web was prepared and then laminated to a 17 g/m² microfiber meltblown web of polypropylene having an average filament diameter of less than 10 micron through spot-bonding using heat and pressure according to U.S. Pat. No. 4,041,203. The laminate had a void volume of 78% and a total basis weight of 37 g/m². The bonded laminate was then saturated using a dip and squeeze size press configuration with a saturant slurry comprised, in percent by weight, of 79.9% of water, 16.7% by weight of an odor-absorbing synthetic zeolite which may be obtained from Union Carbide Corp. under the designation of "ABSCENTS TM", 1.7% by weight of hydroxyethylated modified low viscosity starch which may be obtained from Penford Products Co. under the designation of Penford Gum 330, 1.7% by weight of a non-ionic wetting agent composed of octylphenoxy polyethoxyethanol which contains 9–10 moles of ethylene oxide, the wetting agent being obtained from Rohm & Haas Co. under the designation of "Triton TM X-100". The saturated laminate was then dried by passing the laminate over a steam can with a can pressure of 6 psi.

Upon weighing, it was determined that the dried, saturated laminate had a saturant loading of 26 g/m². That is, the weight of materials adhering to the laminate was 67% by weight of the laminate prior to its passing through the saturant slurry.

EXAMPLE 4

A 96 g/m² bone-dry cellulose web of softwood Kraft paper with a void volume of 77% was saturated using a size pressure configuration. The saturant slurry was comprised, in percent by weight, of 77.4% of water, 16.2% by weight of an odor-absorbing synthetic zeolite which may be obtained from Union Carbide Corp. under the designation of "ABSCENTS TM", 3.2% by weight of sodium bicarbonate, 1.6% by weight of a non-ionic wetting agent obtained from Rohm & Haas Co. under the designation of "Triton TM X-100", and 1.6% by weight of a partially hydrolyzed low viscosity polyvinyl alcohol obtained from Air Products & Chemicals Co., Inc., under the designation of "Vinol TM "205. The saturated web was then dried over a steam can having a can pressure of about 6 psi.

Upon weighing, it was determined that the dried saturated web had a saturant loading of about 28 g/m². That is, the weight of the materials adhering to the web was 29% by weight of the web prior to its passing through the saturant slurry.

The saturated web was then cut into 5"×2" strips and placed in maxi-pads as described in connection with FIG. 4 herein. The resultant pads were tested. The headspace testing showed effective absorption of triethylamine, pyridine, furaldehyde, n-propyl sulfide, and isovaleric acid when analyzed by gas chromatography, the results of which are displayed in Table VII.

TABLE VII

| | Maxi Pads containing the Absorbent System** on a cellulose web of softwood Kraft Paper with or without NaHCO₃ | |
|---|---|---|
| Test Materials Volatiles | Maxi Pad containing synthetic zeolite Absorbent System** on cellulose web of softwood Kraft | Maxi Pad containing synthetic zeolite + NaHCO₃ Absorbent System** on cellulose web of softwood Kraft |
| Triethylamine | 76% | 67% |
| Pyridine | 89% | 91% |
| Furaldehyde | 94% | 100% |
| Isovaleric acid | NR | 85% |
| n-Propyl Sulfide | 71% | 76% |

*NR = No reduction
**Absorbent System = 100 parts synthetic zeolite; 10 parts nonionic wetting agent; 10 parts PVOH in cellulose web of softwood Kraft

EXAMPLE 5

A trilaminate of spunbond/meltblown/spunbond polypropylene was prepared as described in Example 1, with the total basis weight being 37 g/m², and a void volume of 81%. The bonded laminate was then saturated using a dip and squeeze size press configuration with a saturant slurry comprised, in percent by weight, of 77.6% of water, 14.9% of an odor-absorbing synthetic zeolite which may be obtained from Union Carbide Corp. under the designation of "ABSCENTS TM", 3.0% by weight sodium bicarbonate, 3.0% by weight of a partially hydrolyzed polyvinyl alcohol obtained from Air Products & Chemicals Co., Inc., under the designation of "Vinol TM " 205, 1.5% by weight of a non-ionic wetting agent obtained from Rohm & Haas Co. under the designation of "Triton TM X-100". The saturated web was then dried over a steam can having a can pressure of about 6 psi.

Upon weighing, it was determined that the dried saturated web had a saturant loading of 28 g/m². That is, the weight of the material adhering to the laminate was 74% by weight of the laminate prior to its passing through the saturant slurry.

EXAMPLE 6

A trilaminate of spunbond/meltblown/spunbond polypropylene was prepared as described in Example 1, with the total basis weight being 37 g/m². The bonded laminate was then saturated using a dip and squeeze size press configuration with a saturant slurry comprised, in percent by weight, of 77.6% of water, 13.7% of an odor-absorbing synthetic zeolite which may be obtained from Union Carbide Corp. under the designation of "ABSCENTS TM ", 2.7% by weight sodium bicarbonate, 4.5% by weight of a partially hydrolyzed polyvinyl alcohol obtained from Air Products & Chemicals Co., Inc. under the designation of "Vinol" 205 and 1.4% by weight of a non-ionic wetting agent obtained from Rohm & Haas Co. under the designation of "Triton TM X-100". The saturated web was then dried over a steam can having a can pressure of about 6 psi.

Upon weighing, it was determined that the dried saturated web had a saturant loading of 28 g/m². That is, the weight of the material adhering to the laminate was 74% by weight of the laminate prior to its passing through the saturant slurry.

EXAMPLE 7

Two 10 g/m² continuous filament thermoplastic spunbond webs were prepared, and were then laminated to a middle layer constructed of 17 g/m² microfiber meltblown polypropylene web having an average filament diameter of less than 10 microns through spot bonding using heat and pressure according to U.S. Pat. No. 4,041,203. The trilaminate of spunbond/meltblown/spunbond had a total basis weight of 37 g/m². The bonded laminate was then saturated by being dipped into a saturant slurry comprised, in percent by weight, of 77.6% of water, 14.9% of an odor-absorbing synthetic zeolite which may be obtained from Union Carbide Corp. under the designation of "ABSCENTS TM ", 1.4% by weight of a non-ionic wetting agent obtained from Rohm & Haas Co. under the designation of "TRITON TM X-100", 3.0% by weight of a partially hydrolyzed low viscosity polyvinyl alcohol obtained from Air Products & Chemicals Co., Inc., under the designation of "VINOL TM 205", and 3.0% by weight sodium bicarbonate. The treated laminate substrate was then squeezed to remove excess saturant, and then dried using a conventional steam can with a can pressure of 6 psi to produce an odor-absorbent web. The dried and saturated web had a saturant loading of 25 g/m².

The saturated web was then trimmed to 13"×10" and included with treated polypropylene medical fabrics which were sealed in plastic and gamma-sterilized. The resultant package when opened had reduced odor over the medical fabrics without the saturated odor-absorbent material of the present invention.

The headspace of a closed container using 10 in.² of the absorbent web showed effective absorption of triethylamine, pyridine, furaldehyde, n-propyl sulfide and isovaleric acid when analyzed by gas chromatography.

While we have shown and described several embodiments in accordance with the present invention, it is understood that the same is not limited thereto, but is susceptible of numerous changes and modifications as are known to one having ordinary skill in the art, and we therefor do not wish to be limited to the details shown and described herein, but intend to cover all such modifications as are encompassed by the scope of the appended claims.

What is claimed is:

1. A sealed medical product package containing:
   a medical product adapted to be sterilized by gamma irradiation, the product being formed from material which emits odorous substances upon being subjected to gamma irradiation; and
   a web material adapted to absorb the odorous substances caused by gamma radiation or the product the web material comprising:
   a base web having a void volume of greater than about 75 percent;
   a particulate material, adapted to absorb the odorous substances caused by gamma irradiation of the product, distributed generally throughout the base web; and
   a binding system which includes a binding agent and which is transparent to the odorous substances; and
   wherein the particulate material is bound to the base web by the binding system.

2. The medical product package according to claim 1, wherein the package has been subjected to gamma sterilization.

3. The medical product package according to claim 1, wherein the medical product is a hospital gown.

4. The medical product package, according to claim 1, wherein the particulate material comprises a particulate material of an alkaline salt or alkaline earth oxide.

5. The medical product package according to claim 4, wherein the package has been subjected to gamma sterilization.

6. The medical product package according to claim 4, wherein the medical product is a hospital gown.

7. The medical product package according to claim 1, wherein the product is formed from polypropylene.

8. The medical product package according to claim 1, wherein the medical product is formed from polypropylene fibers.

9. The medical product package according to claim 1, wherein the particulate material is selected from the group consisting of one or more molecular sieves, alkaline salts or alkaline earth oxides.

10. The medical product package according to claim 9, wherein the particulate material is a zeolite.

11. The medical product package according to claim 1, wherein the particle size range of the zeolite is from about 1 to about 5 microns.

12. The medical product package according to claim 1, wherein the binding agent comprises a polyvinyl alcohol material.

13. The medical product package according to claim 1, wherein the binding agent comprises a starch material.

14. The medical product package according to claim 1, wherein the binding agent comprises a latex emulsion.

15. The medical product package according to claim 1, wherein the base web is a non-woven sheet of synthetic fibers.

16. The medical product package according to claim 15, wherein the non-woven sheet is a spunbond web.

17. The medical product package according to claim 15, wherein the non-woven sheet is a meltblown web.

18. The medical product package according to claim 15, wherein the non-woven sheet is a spunbonded/meltblown/spunbonded laminate.

19. A sealed hospital gown package containing:

a hospital gown adapted to be sterilized by gamma irradiation, the hospital gown being formed from polypropylene which emits odorous substances upon being subjected to gamma irradiation; and a web material adapted to absorb the odorous substances caused by gamma radiation of the hospital gown, the web material comprising:

a spunbonded/meltblown/spunbonded laminate having a void volume of greater than about 75 percent;

a zeolite material, adapted to absorb the odorous substances caused by gamma irradiation of the hospital gown, distributed generally throughout the laminate; and a binding system which includes a polyvinyl alcohol which is transparent to the odorous substances; and wherein the zeolite material is bound to the laminate by the binding system.

20. The hospital package according to claim 19, wherein the particle size range of the zeolite is from about 1 to about 5 microns.

* * * * *